(12) United States Patent
Drengler et al.

(10) Patent No.: US 8,404,452 B2
(45) Date of Patent: *Mar. 26, 2013

(54) ASSAY FOR IMMUNOSUPPRESSANT DRUGS

(75) Inventors: Susan M. Drengler, Lindenhurst, IL (US); Bennett Wade Baugher, Waukegan, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/410,143

(22) Filed: Mar. 1, 2012

(65) Prior Publication Data

US 2012/0156805 A1 Jun. 21, 2012

Related U.S. Application Data

(63) Continuation of application No. 12/491,330, filed on Jun. 25, 2009, now Pat. No. 8,129,127, which is a continuation of application No. PCT/US2007/088098, filed on Dec. 19, 2007.

(60) Provisional application No. 60/882,863, filed on Dec. 29, 2006.

(51) Int. Cl.
*G01N 33/53* (2006.01)
(52) U.S. Cl. .......................................... 435/7.1; 436/518
(58) Field of Classification Search ........................ None
See application file for complete search history.

(56) References Cited

U.S. PATENT DOCUMENTS

| | | | |
|---|---|---|---|
| 4,108,905 A * | 8/1978 | Wilkinson | 568/454 |
| 4,268,540 A * | 5/1981 | Scott et al. | 427/127 |
| 4,652,517 A | 3/1987 | Scholl et al. | |
| 5,134,875 A | 8/1992 | Jensen et al. | |
| 5,135,875 A | 8/1992 | Meucci et al. | |
| 5,169,773 A | 12/1992 | Rosenthaler et al. | |
| 5,217,971 A | 6/1993 | Takasugi et al. | |
| 5,322,772 A | 6/1994 | Soldin | |
| 5,350,574 A | 9/1994 | Erlanger et al. | |
| 5,354,845 A | 10/1994 | Soldin | |
| 5,426,023 A * | 6/1995 | Uchida | 430/567 |
| 5,489,668 A | 2/1996 | Morrison et al. | |
| 5,498,597 A | 3/1996 | Burakoff et al. | |
| 5,525,523 A | 6/1996 | Soldin | |
| 5,650,228 A | 7/1997 | May | |
| 5,650,288 A | 7/1997 | MacFarlane et al. | |
| 5,698,448 A | 12/1997 | Soldin | |
| 5,750,413 A | 5/1998 | Morrison et al. | |
| 5,780,307 A | 7/1998 | Soldin | |
| 5,876,947 A * | 3/1999 | Kudryk et al. | 435/7.1 |
| 5,897,990 A | 4/1999 | Baumann et al. | |
| 5,955,108 A | 9/1999 | Sutton et al. | |
| 5,990,150 A | 11/1999 | Matsui et al. | |
| 6,054,303 A | 4/2000 | Davalian et al. | |
| 6,087,134 A | 7/2000 | Saunders | |
| 6,187,547 B1 | 2/2001 | Legay et al. | |
| 6,197,588 B1 | 3/2001 | Gray et al. | |
| 6,239,102 B1 | 5/2001 | Tiemessen | |
| 6,328,970 B1 | 12/2001 | Molnar-Kimber et al. | |
| 6,410,340 B1 | 6/2002 | Soldin | |
| 6,541,612 B2 | 4/2003 | Molnar-Kimber et al. | |
| 6,858,439 B1 | 2/2005 | Xu et al. | |
| 6,913,580 B2 | 7/2005 | Stone | |
| 6,998,246 B2 | 2/2006 | Schäffler et al. | |
| 7,189,582 B2 | 3/2007 | Chen et al. | |
| 7,785,898 B2 * | 8/2010 | Bohmer | 436/506 |
| 2002/0002273 A1 | 1/2002 | Sedrani et al. | |
| 2002/0022717 A1 | 2/2002 | Sedrani et al. | |
| 2002/0055124 A1 | 5/2002 | Junda et al. | |
| 2002/0151088 A1 | 10/2002 | Molnar-Kimber et al. | |
| 2003/0157556 A1 | 8/2003 | Maggiore et al. | |
| 2003/0235839 A1 | 12/2003 | McKernan et al. | |
| 2004/0062793 A1 | 4/2004 | Van Dyke | |
| 2004/0101429 A1 | 5/2004 | Ogawa | |
| 2004/0102429 A1 | 5/2004 | Modak et al. | |
| 2005/0033035 A1 | 2/2005 | Beisel et al. | |
| 2005/0055126 A1 | 3/2005 | Genma et al. | |
| 2005/0112778 A1 | 5/2005 | Wang et al. | |
| 2005/0164323 A1 | 7/2005 | Chaudhary et al. | |
| 2005/0272109 A1 | 12/2005 | Schäffler et al. | |
| 2006/0003390 A1 | 1/2006 | Schäffler et al. | |
| 2006/0020401 A1 | 1/2006 | Davis et al. | |
| 2006/0062793 A1 | 3/2006 | Webb et al. | |
| 2006/0216770 A1 | 9/2006 | Kasper et al. | |
| 2006/0257957 A1 | 11/2006 | Drengler et al. | |
| 2008/0020401 A1 | 1/2008 | Grenier et al. | |
| 2008/0160499 A1 | 7/2008 | Grenier et al. | |
| 2008/0176756 A1 | 7/2008 | Siegel et al. | |
| 2009/0325193 A1 | 12/2009 | Grenier et al. | |
| 2009/0325197 A1 | 12/2009 | Drengler et al. | |
| 2009/0325198 A1 | 12/2009 | Holets-McCormack | |

FOREIGN PATENT DOCUMENTS

| | | |
|---|---|---|
| EP | 0440044 A1 | 8/1991 |
| EP | 0471295 | 2/1992 |
| EP | 0693132 B1 | 1/1996 |
| EP | 0753744 A2 | 1/1997 |
| EP | 0293892 | 12/1998 |
| EP | 0973805 A1 | 1/2000 |
| EP | 1244800 B1 | 10/2002 |
| EP | 2118657 A2 | 11/2009 |

(Continued)

OTHER PUBLICATIONS

Alak et al., (Jun. 1997) "Measurement of Tacrolimus (FK506) and Its Metabolites: A Review of Assay Development and Application in Therapeutic Drug Monitoring and Pharmacokinetic Studies", *Therapeutic Drug Monitoring*, 19(3):338-351.

Bose B., et al., (2003) "Characterization and Molecular Modeling of a Highly Stable Anti-Hepatitis B Surface Antigen scFv", *Molecular Immunology*, 40:617-631.

Clarke W., et al., "Immunoassays for therapeutic drug monitoring and clinical toxicology," Drug monitoring and clinical chemistry, 2004, 5, 95-112.

(Continued)

*Primary Examiner* — Jacob Cheu
(74) *Attorney, Agent, or Firm* — Audrey L. Bartnicki; Jennifer Wahlsten, Wearver, Austin, Villeneuve & Sampson LLP

(57) ABSTRACT

The invention provides immunoassays for immunosuppressant drugs, wherein the assay is carried out under high salt conditions to achieve improved sensitivity. The invention also provides kits that are useful for performing the methods of the invention.

28 Claims, 6 Drawing Sheets

FOREIGN PATENT DOCUMENTS

| WO | WO 90/05008 A1 | 5/1990 |
|---|---|---|
| WO | WO 92/18527 A1 | 10/1992 |
| WO | WO 92/19745 A1 | 11/1992 |
| WO | WO 93/25533 A1 | 12/1993 |
| WO | WO 94/24304 A1 | 10/1994 |
| WO | WO 94/25022 A1 | 11/1994 |
| WO | WO 94/25072 A1 | 11/1994 |
| WO | WO 95/16691 A1 | 6/1995 |
| WO | WO 95/25812 A2 | 10/1995 |
| WO | WO 96/12018 A2 | 4/1996 |
| WO | WO 96/13273 A1 | 5/1996 |
| WO | WO 97/03654 A2 | 2/1997 |
| WO | WO 98/00696 A1 | 1/1998 |
| WO | WO 98/45333 A1 | 10/1998 |
| WO | WO 98/53315 A1 | 11/1998 |
| WO | WO 01/34816 A1 | 5/2001 |
| WO | WO 2008/082974 A2 | 7/2008 |
| WO | WO 2008/082979 A2 | 7/2008 |
| WO | WO 2008/082982 A | 7/2008 |
| WO | WO 2008/082984 A2 | 7/2008 |

OTHER PUBLICATIONS

Examination Report of EP Patent Application No. EP07869508, dated Mar. 7, 2012, 8 pages total.

Examination Report of EP Patent Application No. EP07869508, dated Jul. 15, 2011, 6 pages total.

FDA U.S. Food and Drug Administration: "Premarket Notification Architect Sirolimus", 51 O(k) Clearances K070822, Oct. 2007, XP002625226, Retrieved from the Internet: URL:http://www.accessdata.fda.gov/cdrh_docs/pdf7/K070822.pdf.

Hatfield, R.M., et al., (1987) "Development of an Enzyme-Linked Immunosorbent Assay for the Detection of Humoral Antibody to *Pasteurella Anatipestifer*", *Avian Pathology*, 16:123-140.

Kricka et al., (1999) "Human Anti-Animal Antibody Interferences in Immunological Assays", *Clinical Chemistry*, 45(7):942-952.

Kronquist K. E., et al., "Mechanism of alteration of the functional fraction of lipoprotein lipase in rat heart," Life Sci., 1980, 27(13), 1153-1158.

Le Meur Y., et al., "CYP3A5*3 influences sirolimus oral clearance in de novo and stable renal transplant recipients," Clin Pharmacol Ther., 2006, 80(1), 51-60.

Lee J. W., et al., "Tacrolimus (FK506): validation of a sensitive enzyme-linked immunosorbent assay kit for and application to a clinical pharmacokinetic study," Ther Drug Monit., 1997, 19(2), 201-207.

Melnikova, et al., "Antigen Binding Activity of Monoclonal Antibodies After Incubation with Organic Sovents," Biochemistry (Moscow), 2000, vol. 65, No. 11, pp. 1488-1499.

Murakami, et al., "On-chip micro-flow polystyrene bead-based immunoassay for quantitative detection of tacrolimus (FK506)," Analytical Biochemistry, 2004, vol. 334, pp. 111-116.

PCT International Search Report and Written Opinion for Application No. PCT/US07/10076, mailed Jul. 11, 2008, 11 pages total.

PCT International Search Report and Written Opinion for Application No. PCT/US07/88056, mailed Aug. 25, 2008, 11 pages total.

PCT International Search Report and Written Opinion for Application No. PCT/US07/88070, mailed Oct. 8, 2008, 11 pages total.

PCT International Search Report and Written Opinion for Application No. PCT/US07/88087, mailed Sep. 24, 2008, 12 pages total.

PCT International Search Report and Written Opinion for Application No. PCT/US07/88098, mailed May 27, 2008, 7 pages total.

PCT International Search Report and Written Opinion for Application No. PCT/US07/88109, mailed Sep. 24, 2008, 15 pages total.

Simamora et al., "Solubilization of rapamycin." *International Journal of Pharmaceutics* (2001); 213(1-2):25-29.

Sinha, et al., (2002) "Electrostatics in Protein Binding and Function", *Current Protein and Peptide Science*, 3:601-614.

Sinha, et al., (2007) "Understanding antibody-antigen associations by molecular dynamics simulations: Detection of important intra- and inter-molecular salt bridges", *Cell Biochem Biophys*, 47:361-375.

Supplementary European Search Report of EP Patent Application No. EP07869487, dated Mar. 19, 2010, issued Apr. 9, 2010, 8 pages total.

Supplementary European Search Report of EP Patent Application No. EP07865858, dated Mar. 19, 2010, issued Apr. 1, 2010, 9 pages total.

Supplementary European Search Report of EP Patent Application No. EP07869508, dated Mar. 19, 2010, issued Apr. 13, 2010, 11 pages total.

Supplementary European Search Report of EP Patent Application No. EP07861291, dated Jan. 11, 2010, issued Jan. 21, 2010, 11 pages total.

Supplementary European Search Report of EP Patent Application No. 07869499.9, dated Feb. 3, 2011, 6 pages total.

Supplementary European Search Report of EP Patent Application No. 07869484.1, dated Mar. 23, 2011, 8 pages total.

Tamura et al., (Oct. 1987) "A Highly Sensitive Method to Assay FK-506 Levels in Plasma", at pp. 23-29, of "FK-506 A Potential Breakthrough in Immunosuppression", *A Transplantation Proceedings Reprint*, Supplement 6, vol. XIX.

USPTO Office Action dated Aug. 21, 2009, cover sheet and pp. 1-10, Notice of references, Information Disclosure Statement by Application and considered by Examiner in U.S. Appl. No. 11/490,624.

Uwatoko, S., et al., (1984) "Characterization of C1q-Binding IgG Complexes in Systemic Lupus Erythematosus", *Clinical Immunology and Immunopathology*, 30:104-116.

Watson J.D. et al., "The Introduction of Foreign Genes Into Mice", Recombinant DNA, 2nd Ed., W.H. Freeman & Co., New York, 1992, 225-272.

Wilson D., et al., "Multi-center evaluation of analytical performance of the microparticle enzyme immunoassay for sirolimus," Clin Biochem., 2006, 39(4), 378-386.

* cited by examiner

ASSAY FOR IMMUNOSUPPRESSANT DRUGS

CROSS REFERENCE TO RELATED APPLICATIONS

This application is a continuation application U.S. application Ser. No. 12/491,330, filed on Jun. 25, 2009, issued as U.S. Pat. No. 8,129,127 on Mar. 6, 2012, which is a continuation application of PCT International Application PCT/US2007/088098 filed Dec. 19, 2007 (expired), and claims the priority of U.S. Provisional Application Ser. No. 60/882,863 filed Dec. 29, 2006 (expired), all of which are incorporated herein by reference in their entireties for all purposes.

TECHNICAL FIELD

This invention relates to diagnostic immunoassays to determine the concentration levels of an immunosuppressant drug in a test sample, and in particular relates to use of high salt conditions to improve assay sensitivity.

BACKGROUND

Immunosuppressant drugs such as tacrolimus, everolimus, temsorolimus and cyclosporine are effective for the treatment of organ or tissue rejection following transplant surgery, of graft versus host disease and of autoimmune diseases in humans. During immunosuppressant drug therapy, monitoring the blood concentration levels of the immunosuppressant is an important aspect of clinical care because insufficient drug levels lead to graft (organ or tissue) rejection and excessive levels lead to undesired side effects and toxicities. Blood levels of immunosuppressant are therefore measured so drug dosages can be adjusted to maintain the drug level at the appropriate concentration. Diagnostic assays for determination of immunosuppressant blood levels have thus found wide clinical use.

A commonly used competitive format involves the binding of a first antibody to the immunosuppressant and the binding of labeled immunosuppressant (e.g., acridinium-tacrolimus) to the remaining free antibody binding sites, followed by quantitation by detection of the label.

SUMMARY

The invention provides a method for assessing the presence or concentration of an immunosuppressant drug in a test sample. The method entails contacting a test sample or test sample extract with an antibody specific for an immunosuppressant drug under conditions suitable for binding of the antibody to the immunosuppressant drug, if present, to form an assay mixture. Such conditions include a salt concentration of greater than about 0.4 M. Binding of the antibody to the immunosuppressant drug is then detected. In particular embodiments, the immunosuppressant drug is tacrolimus, everolimus, zotarolimus, cyclosporine, or an analog of any of these compounds. In preferred embodiments, tacrolimus or cyclosporine. Conveniently, the test sample includes a human blood sample.

In certain embodiments, the immunoassay is carried out in the presence of salt at a concentration less than or equal to about 4.0 M, e.g., at a concentration of about 2.0 M. In particular, embodiments, the salt includes a monovalent anion, such as chloride. In exemplary embodiments, the salt includes a chloride salt of an alkali metal, such as sodium chloride.

The assay mixture can additionally includes a glycol, such as ethylene glycol, propylene glycol, or an analog thereof, and at least one alcohol having five or fewer carbons. Suitable alcohols include, for example, methanol, ethanol, and propanol. The ratio of glycol to alcohol in the assay mixture can be in the range of about 4:1 to about 1:4, or more particularly, in the range of about 4:1 to about 1:2.

Another aspect of the invention is a test kit, which includes: (a) at least one antibody capable of binding specifically to at least one immunosuppressant drug; (b) an assay diluent including a salt at a concentration of at least about 1.0 M; and (c) a lysis reagent including: a glycol selected from ethylene glycol, propylene glycol, and an analog thereof; and at least one alcohol having five or fewer carbons. In particular embodiments, the immunosuppressant drug is tacrolimus, everolimus, zotarolimus, cyclosporine, or an analog of any of these compounds. In preferred embodiments, tacrolimus or cyclosporine.

In certain embodiments, the concentration of salt in the assay diluent is less than or equal to about 10.0 M, e.g., about 4.5 M. In particular, embodiments, the salt includes a monovalent anion, such as chloride. In exemplary embodiments, the salt includes a chloride salt of an alkali metal, such as sodium chloride.

The test kit can also contain a control composition including the at least one immunosuppressant drug recognized by the antibody provided in the kit.

The alcohol in the lysis reagent can include, for example, methanol, ethanol, and/or propanol. The ratio of glycol to alcohol in the lysis reagent can be in the range of about 4:1 to about 1:4, or more particularly, in the range of about 4:1 to about 1:2.

In an exemplary embodiment, the test kit of the invention includes: (a) at least one antibody or protein capable of binding specifically to at least one immunosuppressant drug selected from the group consisting of tacrolimus and cyclosporine; (b) an assay diluent including a salt at a concentration of at least about 1.0 M; and (c) a lysis reagent comprising: (i) propylene glycol and ethanol at a ratio in the range of about 4:1 to about 1:2; and (ii) a control composition including the at least one immunosuppressant drug of (a).

DETAILED DESCRIPTION

Figure 1:
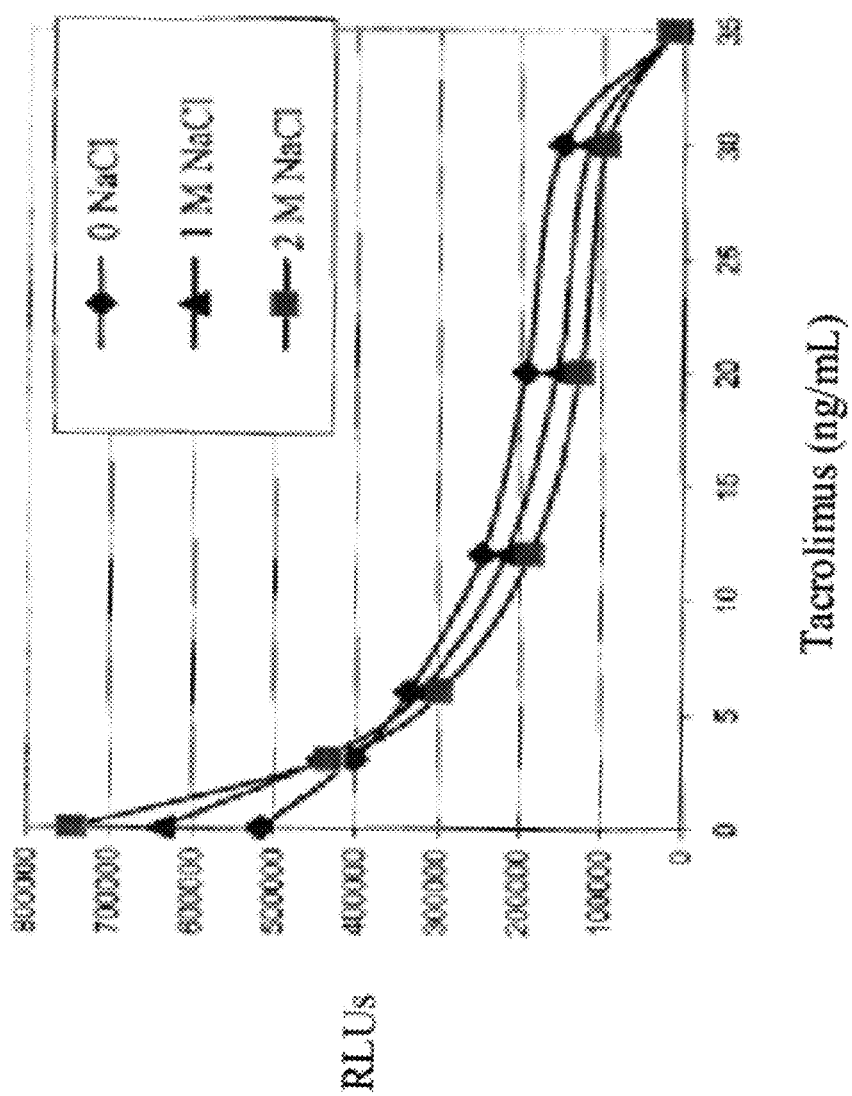
FIG. 1 is a graph obtained using an ARCHITECT® Tacrolimus Assay (Abbott Laboratories, Abbott Park, Ill.) tested with different concentrations of NaCl in the reaction. Abscissa: tacrolimus amount (ng/mL). Ordinate: signal (Relative light units, or RLUs). Symbols: (solid diamond), 0 M NaCl; (solid triangle), 1M NaCl; (solid square), 2 M NaCl.

The invention relates to immunoassays for immunosuppressant drugs that are carried out under high salt conditions to improve assay sensitivity. This improvement is not attributable to a decrease in non-specific binding. Rather, high salt is believed to increase the drug-antibody interaction.

DEFINITIONS

Terms used in the claims and specification are defined as set forth below unless otherwise specified.

An "immunosuppressant drug" or "immunosuppressant", as used herein, refers to a therapeutic compound, either small molecule or antibody based, that has the same or similar chemical structure to either tacrolimus, or cyclosporine, also known as cyclosporine A. Any known or hereafter developed analog of either tacrolimus or cyclosporine is considered an immunosuppressant herein. Preferred immunosuppressants include tacrolimus, everolimus, temsorolimus, zotarolimus and cyclosporine. Tacrolimus and cyclosporine are calcineurin inhibitors that suppress early activation of the immune system's T lymphocytes through inhibition of cytokines such as interleukin 2. In contrast, the primary target of everolimus and zotarolimus is mammalian target of rapamycin (mTOR), a specific cell-cycle regulatory protein. The inhibition of mTOR leads to suppression of cytokine-driven T-lymphocyte proliferation.

The chemical formula of cyclosporine is in Formula A. The chemical formula of sirolimus (rapamycin) is in Formula B. The chemical formula of the structural difference of everolimus (RAD) from sirolimus is in Formula C.

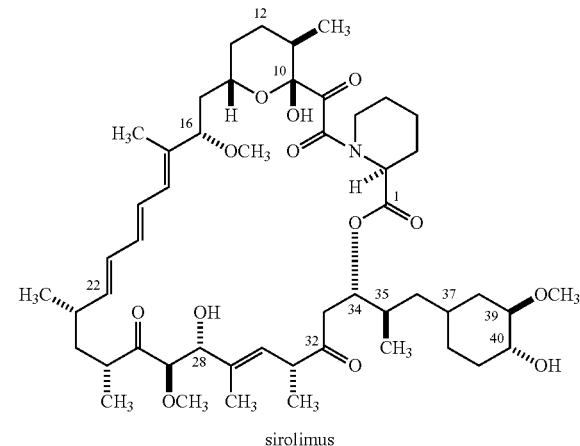

sirolimus

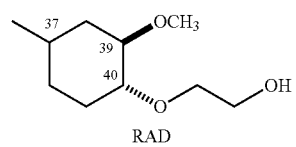

RAD

Numerous derivatives or analogs of cyclosporine have been prepared. The invention comprises assays and assay kits for cyclosporine or any of its analogs.

Tacrolimus, also known as FK-506, was isolated from a strain of *S. tsukubaensis*. FK-506's chemical formula is published in European Patent EP 0 293 892 B1. Analogs of FK-506 include the related natural products FR-900520 and FR-900523, which differ from FK-506 in their alkyl substituent at C-21, and were isolated from *S. hygroscopicus* yakushimnaensis. Another analog, FR-900525, produced by *S. tsukubaensis*, differs from FK-506 in the replacement of a pipecolic acid, moiety with a proline group. The invention comprises assays and assay kits for FK-506 or any of its analogs.

ABT-578 [40-epi-(1-tetrazolyl)-rapamycin], known better today as zotarolimus, is a semi-synthetic macrolide triene antibiotic derived from rapamycin. Zotarolimus' structure is shown in Formula D.

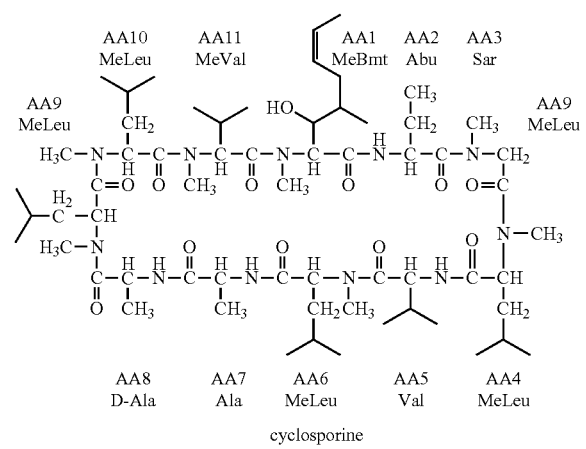

cyclosporine

The isomers of zotarolimus

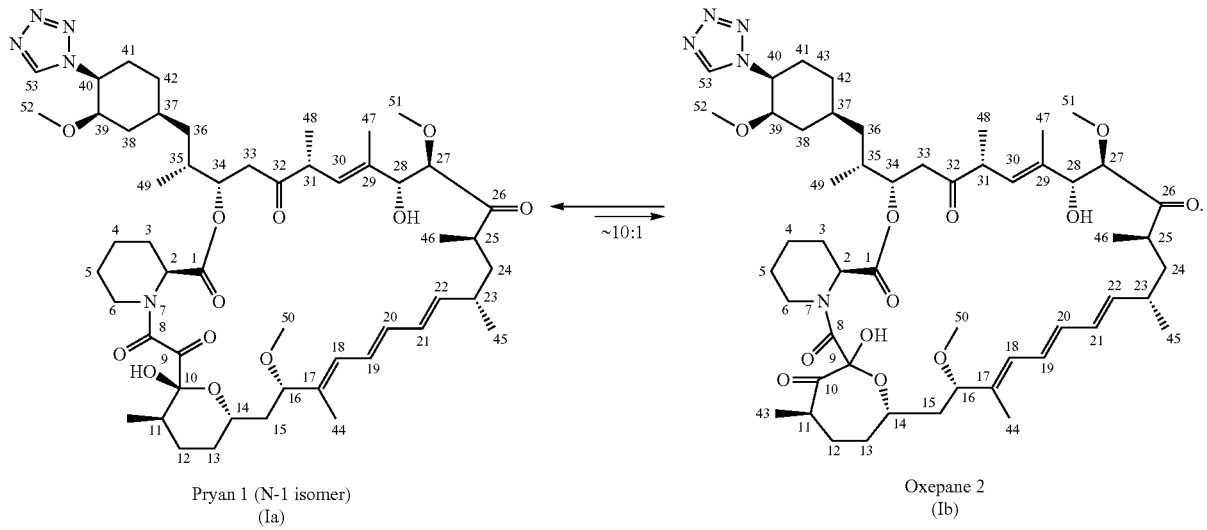

Pryan 1 (N-1 isomer)
(Ia)

Oxepane 2
(Ib)

Formula D

The term "test sample" refers to a component, tissue or fluid of an animal's body that is the source of the immunosuppressant drug analyte. These components, tissues and fluids include human and animal body fluids such as whole blood, serum, plasma, synovial fluid, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens; and fixed cell specimens. Preferably, the test sample is a human peripheral blood sample. The term "test sample" includes test samples that have had one or more reagents, such as, e.g., a lysis reagent, added thereto.

The term "test sample extract" refers to a test sample in which one or more components have been separated from one or more additional components. In test sample extracts according to the invention, the immunosuppressant drug has been separated from one or more carrier proteins.

As used herein, an "antibody" refers to a protein consisting of one or more polypeptides substantially encoded by immunoglobulin genes or fragments of immunoglobulin genes. This term encompasses polyclonal antibodies, monoclonal antibodies, and fragments thereof, as well as molecules engineered from immunoglobulin gene sequences. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain (VL)" and "variable heavy chain (VH)" refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab')2, a dimer of Fab which itself is a light chain joined to VH-CH1 by a disulfide bond. The F(ab')2 may be reduced under mild conditions to break the disulfide linkage in the hinge region thereby converting the (Fab')$_2$ dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology.

Thus, the term "antibody," as used herein, also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv), in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker (Huston, et al. (1988) Proc. Nat. Acad. Sci. USA, 85: 5879-5883). While the VH and VL are connected to each as a single polypeptide chain, the VH and VL domains associate non-covalently. The scFv antibodies and a number of other structures convert the naturally aggregated, but chemically separated, light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778).

"Analyte," as used herein, refers to the substance to be detected, which may be suspected of being present in the test sample. The analyte can be any substance for which there exists a naturally occurring specific binding partner or for which a specific binding partner can be prepared. Thus, an analyte is a substance that can bind to one or more specific binding partners in an assay.

A "binding partner," as used herein, is a member of a binding pair, i.e., a pair of molecules wherein one of the molecules binds to the second molecule. Binding partners that bind specifically are termed "specific binding partners." In addition to the antigen and antibody binding partners commonly used in immunoassays, other specific binding partners can include biotin and avidin, carbohydrates and lectins, complementary nucleotide sequences, effector and receptor molecules, cofactors and enzymes, enzyme inhibitors and enzymes, and the like. Immunoreactive specific binding partners include antigens, antigen fragments, antibodies and antibody fragments, both monoclonal and polyclonal, and complexes thereof, including those formed by recombinant DNA methods.

The term "specific binding" is defined herein as the preferential binding of binding partners to another (e.g., two polypeptides, a polypeptide and nucleic acid molecule, or two nucleic acid molecules) at specific sites. The term "specifically binds" indicates that the binding preference (e.g., affinity) for the target molecule/sequence is at least 2-fold, more preferably at least 5-fold, and most preferably at least 10- or 20-fold over a non-specific target molecule (e.g., a randomly generated molecule lacking the specifically recognized site(s)).

An antibody that specifically binds an immunosuppressant drug is said to be "specific for" that immunosuppressant drug.

The term "capture agent" is used herein to refer to a binding partner that binds to analyte, preferably specifically. Capture agents can be attached to a solid phase. As used herein, the binding of a solid phase-affixed capture agent to analyte forms a "solid phase-affixed complex."

The term "labeled detection agent" is used herein to refer to a binding partner that binds to analyte, preferably specifically, and is labeled with a detectable label or becomes labeled with a detectable label during use in an assay.

A "detectable label" includes a moiety that is detectable or that can be rendered detectable.

As used with reference to a labeled detection agent, a "direct label" is a detectable label that is attached, by any means, to the detection agent.

As used with reference to a labeled detection agent, an "indirect label" is a detectable label that specifically binds the detection agent. Thus, an indirect label includes a moiety that is the specific binding partner of a moiety of the detection agent.

Biotin and avidin are examples of such moieties that are employed, for example, by contacting a biotinylated antibody with labeled avidin to produce an indirectly labeled antibody.

As used herein, the term "indicator reagent" refers to any agent that is contacted with a label to produce a detectable signal. Thus, for example, in conventional enzyme labeling, an antibody labeled with an enzyme can be contacted with a substrate (the indicator reagent) to produce a detectable signal, such as a colored reaction product.

As used herein, a "glycol analog" is any glycol having from two to six carbon atoms.

I. Sample Collection and Processing

The assay methods of the invention are generally carried out on test samples derived from an animal, preferably a mammal, and more preferably a human.

The methods of the invention can be carried out using any sample that may contain the immunosuppressant drug. Convenient samples include, for example, blood, serum, and plasma.

In particular embodiments, the immunosuppressant is typically separated from the other components of the sample. The bulk of the immunosuppressant drug in the sample is present in a complex with various "carrier" molecules, such as binding proteins. Tacrolimus and cyclosporine are found predominately in the red blood cells of patient specimens and are associated with specific binding proteins, FKBP for tacrolimus, and cyclophilin for cyclosporine. To ensure an accurate measurement of the total drug concentration in the specimen, the drug bound to the binding proteins is preferably liberated prior to quantitation.

Separation of immunosuppressant drugs from their binding proteins in blood can be accomplished by treatment with organic solvents, such as, acetonitrile, methanol, or diethyl ether. These solvents denature the binding proteins and liberate the drug. Methanol has typically been employed to extract tacrolimus or cyclosporine from blood specimens before immunoassay. The methanol concentration is generally sufficient to liberate the drug from the binding protein, but not so great as to interfere with the subsequent immunoassay.

In certain embodiments, immunosuppressant drugs can be separated using an extractive reagent composition that yields a sample extract that is compatible with immunoassay components and has low vapor pressure. A low-vapor pressure (e.g., lower than that of water) is advantageous to reduce evaporation of the extract containing the immunosuppressant, which can cause inaccuracy in the measurement of the drug concentration. This extractive reagent composition is described in the commonly owned, co-pending application U.S. Nonprovisional application Ser. No. 11/490,624 filed on Jul. 21, 2006, and is explicitly incorporated by reference in its entirety for its teachings regarding same. Briefly, the extractive reagent composition includes dimethyl sulfoxide (DMSO), at least one divalent metal salt and water. In particular embodiments, the extractive reagent composition includes DMSO and at least one of zinc sulfate, zinc acetate, zinc nitrate, zinc chloride, cadmium sulfate, copper sulfate and mixtures of two or more of these metal salts. A more preferred extractive reagent composition includes DMSO, the metal salt and at least one glycol having from two to six carbon atoms, which is preferably at least one of ethylene glycol (EG), propylene glycol (PG) or mixtures of EG and PG.

The DMSO concentration, when used without EG or PG, in the extractive reagent composition is at least 50%, and preferably at least 80%, up to about 95% by volume of the extractive reagent composition. The metal salt concentration is at least 5 mM, and concentrations up to 400 mM can be used. A preferred concentration range for the zinc salt is 30-75 mM. Use of high salt concentrations, for example above about 75 mM, may require use of a chelating compound, such as ethylene diamine tetraacetic acid, in a subsequent assay step to remove the excess metal. The extractive reagent compositions are made by any suitable mixing method to sufficiently mix the DMSO with water and dissolve the metal salt.

When EG or PG is included in the extractive reagent composition, lower concentrations of DMSO are more effective. In such compositions, EG, PG or mixtures thereof are present in a concentration of at least 18%, and preferably about 25% to about 33% by volume of the extractive reagent composition, and DMSO is present in a concentration of at least 50% by volume of the extractive reagent composition.

The sample extract is formed by any mixing technique at any desirable temperature to contact any chosen amount of the sample with the extractive reagent composition. For example, about 100 μL to about 600 μL of blood sample can be mixed with about 200 μL to about 12004 of the extractive reagent composition for up to about five minutes. In certain embodiments, the extraction of the immunosuppressant is accomplished by mixing 150 μL of blood sample with 300 μL of composition and vortexing vigorously for 5-10 seconds. In variations of such embodiments, the extraction can be carried out by heating the mixture to a temperature above room temperature in the range of about 30 degrees centigrade to about 50 degrees centigrade for about five minutes to about sixty minutes. After mixing, the resulting suspension is centrifuged for a suitable time at a suitable revolution rate to produce a supernatant phase and a precipitant phase. For example, the mixture can be centrifuged at 13,000 rpm for 5 minutes to pellet the precipitant. After the centrifugation, the supernatant is separated using any suitable method. The supernatant is then assayed for the immunosuppressant using an immunoassay according to the invention.

In other embodiments, immunosuppressant drugs can be separated using a lysis reagent, preferably followed by an additional agent that releases the drug from any associated binding proteins. An exemplary lysis reagent includes a glycol having from two to six carbon atoms. At least one alcohol having five or fewer carbons is included in the lysis reagent or added to the lysis mixture. Glycols suitable for use in the lysis reagent include, for example, EG, PG, and analogs thereof, as well as mixtures of such glycols. Alcohols suitable for use in the invention include, for example, methanol, ethanol, propanol, and mixtures thereof. In particular embodiments, the ratio of glycol to alcohol is in the range of about 5:1 to about 1:5, 4:1 to about 1:4, 2:1 to about 1:2, or about 1:1 (volume:volume). In more particular embodiments, the ratio of glycol to alcohol is in the range of about 4:1 to about 1:2.

The lysis mixture can be formed by any mixing technique at any desirable temperature to contact any chosen amount of the sample with the lysis reagent. The sample is contacted with a sufficient volume of lysis reagent to lyse the cells in the sample and produce a homogeneous mixture. For a lysis reagent wherein the ratio of glycol to alcohol is in the range of about 4:1 to about 1:4, as described above, sample can be added to the lysis reagent at a ratio in the range of about 2:1 to about 1:2, about 1:3, about 1:4, about 1:5, or about 1:10; e.g., about 1:1 (volume:volume), or any other range including these values as endpoints, depending on the lysis reagent composition. In preferred embodiments, lysis is complete in less than a minute at room temperature.

When a lysis reagent is employed, the immunosuppressant drug can be released from binding protein(s) using, for example, a releasing agent that competes with the drug for binding to the binding protein(s). The agent is generally selected so that it will not affect the results of the assay to be carried out, e.g., the agent is typically one that the relevant antibody or antibodies does/do not cross-react with. For example, the agent can be a different, but structurally similar, immunosuppressant drug, if the antibody used in the subsequent immunoassay distinguishes between sirolimus and tacrolimus. U.S. Pat. No. 6,187,547 (issued Feb. 13, 2001 to Legay and Wenger; incorporated herein by reference in its entirety for its teachings regarding immunosuppressant drug competition) describes "binding competitors" useful for releasing immunosuppressant drugs from binding proteins. Examples include: [Thr$^2$, Leu$^5$, D-Hiv$^8$, Leu$^{10}$]-Ciclosporin, which can release cyclosporine.

Alternatively, a protease can be employed to release the analyte from binding protein(s). Exemplary proteases include proteinase K, subtilisin, dispase, thermolysin, trypsin, ficin, bromelain, and combinations thereof. Described in co-pending application U.S. Nonprovisional Application Ser. No. 60/882,732 filed on Dec. 29, 2006, which is explicitly incorporated by reference in its entirety for its teachings regarding same.

After lysis of the sample, the resulting lysis mixture can be analyzed by immunoassay.

II. Immunoassay of Immunosuppressant Drugs

A. In General

Immunoassays according to the invention can be used for the qualitative identification and/or the quantification of the immunosuppressant drug in a test sample. These methods are applicable, for example, to immunoassays of tacrolimus, everolimus, zotarolimus, cyclosporine, and analogs of any of these compounds. In certain embodiments, immunoassays for immunosuppressant drugs are carried out by combining an extractive reagent composition with the test sample and water to form a test sample extract. The test sample or test sample extract is contacted with at least one antibody specific for the immunosuppressant drug under conditions suitable for binding of the antibody to the immunosuppressant drug, if present, to form an assay mixture, and binding of the antibody to the immunosuppressant drug is detected.

Enhanced assay sensitivity can be generally achieved by contacting the test sample or test sample extract with the antibody in the presence of a salt concentration of greater than about 0.4 M (e.g., from about 0.5 M to about 5.0 M). In particular embodiments, the salt concentration is less than or equal to about 4.0 M (e.g., from about 0.5 M to about 4.0 M). In exemplary embodiments, the salt concentration is about 2.0 M (e.g., from about 1.5 M to about 2.5 M, particularly about 1.8 M, about 1.9 M, about 2.0 M, about 2.1 M, or about 2.2 M). Suitable salts can include, for example, any of the following anions: fluoride, chloride, bromide, iodide, thiocyanate, acetate, citrate, and bisulfate. In particular embodiments, the salt includes a monovalent anion, such as, for example: fluoride, chloride, bromide, iodide, thiocyanate, and acetate. In preferred embodiments, the salt includes chloride, e.g., a chloride salt of an alkali metal (e.g., lithium, sodium, potassium, rubidium, cesium). Generally, the salt employed is soluble under the assay conditions. Sodium chloride is highly soluble under most conditions, and can thus be conveniently used to enhance assay sensitivity in a wide variety of immunoassays according to the invention.

The salt can be provided to the assay mixture in any convenient manner and can be present before, or added after, contact between the test sample or test sample extract and the antibody. In particular embodiments, the salt is provided in an assay diluent, which can also optionally include one or more other components, in addition to water (such as, for example, a buffer). The salt concentration in the assay diluent will vary, depending on the desired final salt concentration and on the amount of diluent added to the assay mixture. For example, an assay diluent having a salt concentration of about 4.0 M could be added to an equal volume of assay mixture to provide a final salt concentration of 2.0 M.

B. Antibodies

In immunoassays for the qualitative detection of an immunosuppressant drug in a test sample, at least one antibody that binds to the immunosuppressant drug is contacted with at least one test sample or test sample extract suspected of containing drug to form an antibody-drug immune complex. Any suitable antibodies that bind to the particular immunosuppressant can be used in immunoassay according to the invention. Antibodies to each of tacrolimus, zotarolimus, cyclosporine and everolimus are known in the art and/or are commercially available, and any of these can be used.

An exemplary protocol for producing an antibody specific for an immunosuppressant drug is as follows. Female RBf/Dnj mice are administered 3 monthly boosts of a drug-27-CMO-tetanus toxoid immunogen followed by an immunization with drug-42-HS-tetanus toxoid preparation on the 4th month. Seven months later, an intrasplenic pre-fusion boost is administered to the animal using the drug-27-CMO-tetanus toxoid immunogen 3 days prior to the fusion. Splenic B-cells are then isolated and used in a standard polyethylene (PEG) fusion with the SP2/0 myeloma. Confluent cultures are screened for anti-drug activity 10-14 days later in a microtiter EIA and positive cultures are then cloned using limiting dilution cloning technique. The resulting clones are isolated and scaled up in IMDM w/FBS (Invitrogen Corp., Carlsbad, Calif.) tissue culture medium and the secreted antibody is affinity purified using Protein A. An exemplary, preferred antibody generated using sirolimus as the drug can be used in immunoassays for everolimus and zotarolimus.

An exemplary, preferred antibody for use in immunoassays for tacrolimus is described in M. Kobayashi et al., "A Highly Sensitive Method to Assay FK-506 Levels in Plasma", at pp 23-29 of "FK-506 A Potential Breakthrough in Immunosuppression", *A Transplantation Proceedings Reprint*, Supplement 6, Vol. XIX, October, 1987, Editors T. Starzl, L. Makowka and S. Todo, published by Grune & Stratton, Inc., Philadelphia, Pa.

An exemplary, preferred antibody for use in immunoassays for cyclosporine is the monoclonal antibody that is a component of Abbott Laboratories' commercially available AxSym cyclosporine assay for measuring cyclosporine.

C. Detection

The antibody-drug immune complexes can then detected using any suitable technique. For example, an antibody can be labeled with a detectable label to detect the presence of the antibody-drug complex. The selection of a particular label is not critical, but the chosen label must be capable of producing a detectable signal either by itself or in conjunction with one or more additional substances.

Useful detectable labels, their attachment to antibodies and detection techniques therefore are known in the art. Any detectable label known in the art can be used. For example, the detectable label can be a radioactive label, such as, $^{3}H$, $^{125}I$, $^{35}S$, $^{14}C$, $^{32}P$, $^{33}P$; an enzymatic label, such as horseradish peroxidase, alkaline peroxidase, glucose 6-phosphate dehydrogenase, etc.; a chemiluminescent label, such as, acridinium derivatives, luminol, isoluminol, thioesters, sulfonamides, phenanthridinium esters, etc.; a fluorescent label, such as, fluorescein (5-fluorescein, 6-carboxyfluorescein, 3'6-carboxyfluorescein, 5(6)-carboxyfluorescein, 6-hexachlorofluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, *Introduction to Immunocytochemistry*, $2^{nd}$ ed., Springer Verlag, N.Y. (1997) and in Haugland, *Handbook of Fluorescent Probes and Research Chemi* (1996), which is a combined handbook and catalogue published by Molecular Probes, Inc., Eugene, Oreg., each of which is incorporated herein by reference. Preferred labels for use with the invention are chemiluminescent labels such as acridinium-9-carboxamide. Additional detail can be found in Mattingly, P. G., and Adamczyk, M. (2002) Chemiluminescent N-sulfonylacridinium-9-carboxamides and their application in clinical assays, in *Luminescence Biotechnology: Instruments and Applications* (Dyke, K. V., Ed.) pp 77-105, CRC Press, Boca Raton.

The detectable label can be bound to the analyte, analyte analog, or antibody either directly or through a coupling agent. An example of a coupling agent that can be used is EDAC (1-ethyl-3-(3-dimethylaminopropyl) carbodiimide, hydrochloride), which is commercially available from Sigma-Aldrich (St. Louis, Mo.). Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, N10-(3-sulfopropyl)-N-(3-carboxypropyl)-acridinium-9-carboxamide, otherwise known as CPSP-Acridinium Ester or N10-(3-sulfopropyl)-N-(3-sulfopropyl)-acridinium-9-carboxamide, otherwise known as SPSP-Acridinium Ester.

Alternatively, a second antibody that binds to immunosuppressant and that contains a detectable label can be added to the test sample or test sample extract and used to detect the presence of the antibody-drug complex. Any suitable detectable label can be used in this embodiment.

D. Exemplary Formats

The immunoassays of the invention can be conducted using any format known in the art, such as, but not limited to, a sandwich format, a competitive inhibition format (including both forward or reverse competitive inhibition assays) or a fluorescence polarization format.

In immunoassays for the quantitative detection of an immunosuppressant, such as a preferred sandwich type format, at least two antibodies are employed to separate and quantify the drug in the test sample or test sample extract. More specifically, the at least two antibodies bind to different parts of the drug, forming an immune complex which is referred to as a "sandwich". Generally, one or more antibodies can be used to capture the immunosuppressant in the test sample (these antibodies are frequently referred to as a "capture" antibody or "capture" antibodies) and one or more antibodies are used to bind a detectable (namely, quantifiable) label to the sandwich (these antibodies are frequently referred to as the "detection" antibody or "detection" antibodies). In a sandwich assay, it is preferred that both antibodies binding to the drug are not diminished by the binding of any other antibody in the assay to its respective binding site. In other words, antibodies should be selected so that the one or more first antibodies brought into contact with a test sample or test sample extract suspected of containing an immunosuppressant do not bind to all or part of the binding site recognized by the second or subsequent antibodies, thereby interfering with the ability of the one or more second or subsequent antibodies to bind to the drug. In a sandwich assay, the antibodies, and preferably, the at least one capture antibody, are used in molar excess amounts relative to the maximum amount of drug expected in the test sample or test sample extract. For example, from about 5 µg/mL to about 1 mg/mL of antibody per mL of solid phase containing solution can be used.

In one embodiment, the at least one first capture antibody can be bound to a solid support which facilitates the separation of the first antibody-drug complex from the test sample. The solid support or "solid phase" used in the inventive immunoassay is not critical and can be selected by one skilled in the art. A solid phase or solid support, as used herein, refers to any material that is insoluble, or can be made insoluble by a subsequent reaction. Useful solid phases or solid supports are known to those in the art and include the walls of wells of a reaction tray, test tubes, polystyrene beads, magnetic beads, nitrocellulose strips, membranes, microparticles such as latex particles, sheep (or other animal) red blood cells, and Duracytes® (a registered trademark of Abbott Laboratories, Abbott Park, Ill.), which are red blood cells "fixed" by pyruvic aldehyde and formaldehyde, and others. Suitable methods for immobilizing peptides on solid phases include ionic, hydrophobic, covalent interactions and the like. The solid phase can be chosen for its intrinsic ability to attract and immobilize the capture agent. Alternatively, the solid phase can comprise an additional receptor that has the ability to attract and immobilize the capture agent. The additional receptor can include a charged substance that is oppositely charged with respect to the capture agent itself or to a charged substance conjugated to the capture agent. As yet another alternative, the receptor can be any specific binding partner which is immobilized upon (attached to) the solid phase and which has the ability to immobilize the capture agent through a specific binding reaction. The receptor molecule enables the indirect binding of the capture agent to a solid phase material before the performance of the assay or during the performance of the assay.

Any solid support known in the art can be used, including but not limited to, solid supports made out of polymeric materials in the forms of wells, tubes or beads. The antibody (or antibodies) can be bound to the solid support by adsorption, by covalent bonding using a chemical coupling agent or by other means known in the art, provided that such binding does not interfere with the ability of the antibody to bind the drug. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

It is within the scope of the present invention that the solid phase also can comprise any suitable porous material with sufficient porosity to allow access by detection antibodies and a suitable surface affinity to bind antigens. Microporous structures generally are preferred, but materials with the gel structure in the hydrated state may be used as well. Such useful solid supports include but are not limited to nitrocellulose and nylon. It is contemplated that such porous solid supports described herein preferably are in the form of sheets of thickness from about 0.01 to 0.5 mm, preferably about 0.1 mm. The pore size may vary within wide limits, and preferably is from about 0.025 to 15 microns, especially from about 0.15 to 15 microns. The surface of such supports may be activated by chemical processes that cause covalent linkage of the antigen or antibody to the support. The irreversible binding of the antigen or antibody is obtained, however, in general, by adsorption on the porous material by hydrophobic forces.

After the test sample extract suspected of containing or containing the immunosuppressant is brought into contact with the at least one first capture antibody, the resulting mixture is incubated to allow for the formation of a first capture antibody (or multiple antibody)-drug complex. The incubation can be carried out at any suitable pH, including a pH of from about 4.5 to about 10.0, at any suitable temperature, including from about 2° C. to about 45° C., and for a suitable time period from at least about one (1) minute to about eighteen (18) hours, preferably from about 4-20 minutes, most preferably from about 17-19 minutes.

After the addition of a detection agent and the formation of a labeled complex, the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. Once the amount of the label in the complex has been quantified, the concentration of drug in the test sample can be determined by use of a standard curve that has been generated, for example, using serial dilutions of immunosuppressant drug of known concentration. Other than using serial dilutions of the drug, the standard curve can be generated gravimetrically, by mass spectroscopy and by other techniques known in the art.

In a preferred forward competitive format, an aliquot of labeled drug, or analogue thereof, of a known concentration is used to compete with the drug present in a test sample for binding to the antibody. In a forward competition assay, an immobilized antibody can either be sequentially or simultaneously contacted with the test sample and a labeled drug or drug analogue thereof. The drug or drug analogue can be labeled with any suitable detectable label, including those detectable labels discussed above. In this assay, the capture antibody can be immobilized on to a solid support using the techniques discussed previously herein. Alternatively, the capture antibody can be coupled to an antibody, such as an antispecies antibody, that has been immobilized on to a solid support, such as a microparticle.

The labeled drug or drug analogue, the test sample extract and the antibody are incubated under conditions similar to those described above in connection with the sandwich assay format. Two different types of antibody-drug complexes are then generated. Specifically, one of the antibody-drug complexes generated contains a detectable label while the other antibody-drug complex does not contain a detectable label. The antibody-drug complex can be, but does not have to be, separated from the remainder of the test sample extract prior to quantification of the detectable label. Regardless of whether the antibody-drug complex is separated from the remainder of the test sample, the amount of detectable label in the antibody-drug complex is then quantified. The concentration of drug in the test sample can then be determined by comparing the quantity of detectable label in the antibody-drug complex to a standard curve. The standard curve can be generated using serial dilutions of the drug of known concentration, by mass spectroscopy, gravimetrically and by other techniques known in the art.

The antibody-drug complex can be separated from the test sample by binding the antibody to a solid support, such as the solid supports discussed above in connection with the sandwich assay format, and then removing the remainder of the test sample from contact with the solid support.

In a reverse competition assay, an immobilized immunosuppressant drug or analogue thereof can either be sequentially or simultaneously contacted with a test sample or test sample extract and at least one labeled antibody. The antibody can be labeled with any suitable detectable label, including those detectable labels discussed above. The drug or drug analogue can be bound to a solid support, such as the solid supports discussed above in connection with the sandwich assay format.

The immobilized drug or drug analogue, test sample or test sample extract, and at least one labeled antibody are incubated under conditions similar to those described above in connection with the sandwich assay format. Two different types of antibody-drug complexes are then generated. Specifically, one of the antibody-drug complexes generated is immobilized and contains a detectable label while the other antibody-drug complex is not immobilized and contains a detectable label. The non-immobilized antibody-drug complex and the remainder of the test sample or test sample extract are removed from the presence of the immobilized antibody-drug complex through techniques known in the art, such as washing. Once the non-immobilized antibody-drug complex is removed, the amount of detectable label in the immobilized antibody-drug complex is then quantified. The concentration of drug in the test sample can then be determined by comparing the quantity of detectable label in the antibody-drug complex to a standard curve. The standard curve can be generated using serial dilutions of the drug of known concentration, by mass spectroscopy, gravimetrically and by other techniques known in the art.

In a fluorescence polarization assay, in one embodiment, an antibody or functionally active fragment thereof is first contacted with an unlabeled test sample containing the immunosuppressant drug to form an unlabeled antibody-drug complex. The unlabeled antibody-drug complex is then contacted with a fluorescently labeled drug or analogue thereof. The labeled drug or drug analogue competes with any unlabeled drug in the test sample for binding to the antibody or functionally active fragment thereof. The amount of labeled antibody-drug complex formed is determined and the amount of drug in the test sample determined via use of a standard curve.

The use of scanning probe microscopy (SPM) for immunoassays also is a technology to which the immunoassay methods of the present invention are easily adaptable. In SPM, in particular in atomic force microscopy, the capture agent is affixed to a solid phase having a surface suitable for scanning. The capture agent can, for example, be adsorbed to a plastic or metal surface. Alternatively, the capture agent can be covalently attached to, e.g., derivatized plastic, metal, silicon, or glass according to methods known to those of ordinary skill in the art. Following attachment of the capture agent, the test sample is contacted with the solid phase, and a scanning probe microscope is used to detect and quantify solid phase-affixed complexes. The use of SPM eliminates the need for labels which are typically employed in immunoassay systems. Such a system is described in U.S. Pat. No. 662,147, which is incorporated herein by reference.

Immunoassays according to the invention can also be carried out using a MicroElectroMechanical System (MEMS). MEMS are microscopic structures integrated onto silicon that combine mechanical, optical, and fluidic elements with electronics, allowing convenient detection of an analyte of interest. An exemplary MEMS device suitable for use in the invention is the Protiveris' multicantilever array. This array is based on chemo-mechanical actuation of specially designed silicon microcantilevers and subsequent optical detection of the microcantilever deflections. When coated on one side with a binding partner, a microcantilever will bend when it is exposed to a solution containing the complementary molecule. This bending is caused by the change in the surface energy due to the binding event. Optical detection of the degree of bending (deflection) allows measurement of the amount of complementary molecule bound to the microcantilever.

In other embodiments, immunoassays according to the invention are carried out using electrochemical detection. A basic procedure for electrochemical detection has been described by Heineman and coworkers. This entailed immobilization of a primary antibody (Ab, rat-anti mouse IgG), followed by exposure to a sequence of solutions containing the antigen (Ag, mouse IgG), the secondary antibody conjugated to an enzyme label (AP-Ab, rat anti mouse IgG and alkaline phosphatase), and p-aminophenyl phosphate (PAPP). The AP converts PAPP to p-aminophenol ($PAP_R$, the "R" is intended to distinguish the reduced form from the oxidized form, $PAP_O$, the quinoneimine), which is electrochemically reversible at potentials that do not interfere with reduction of oxygen and water at pH 9.0, where AP exhibits optimum activity. $PAP_R$ does not cause electrode fouling, unlike phenol whose precursor, phenylphosphate, is often used as the enzyme substrate. Although $PAP_R$ undergoes air and light oxidation, these are easily prevented on small scales and short time frames. Picomole detection limits for $PAP_R$ and femtogram detection limits for IgG achieved in microelectrochemical immunoassays using PAPP volumes ranging from 20 µL to 360 µL have been reported previously. In capillary immunoassays with electrochemical detection, the lowest detection limit reported thus far is 3000 molecules of mouse IgG using a volume of 70 µL and a 30 minute or a 25 minute assay time.

Various electrochemical detection systems are described in U.S. Pat. No. 7,045,364 (issued May 16, 2006; incorporated herein by reference), U.S. Pat. No. 7,045,310 (issued May 16, 2006; incorporated herein by reference), U.S. Pat. No. 6,887,714 (issued May 3, 2005; incorporated herein by reference), U.S. Pat. No. 6,682,648 (issued Jan. 27, 2004; incorporated herein by reference); U.S. Pat. No. 6,670,115 (issued Dec. 30, 2003; incorporated herein by reference).

In particular embodiments, useful, for example, for simultaneously assaying multiple analytes in one test sample, the solid phase can include a plurality different capture agents. Thus, for example, the solid phase can have affixed thereon a plurality of antibodies, wherein each is intended to test for the presence of different analytes in the sample. In an exemplary embodiment, the solid phase can consist of a plurality of different regions on a surface, wherein each region has a particular antibody affixed therein.

Multiplex formats can, but need not, employ a plurality of labels, wherein each label is used for the detection of a particular analyte. For example, multiple, different analytes can be detected without using a plurality of labels where a plurality of capture agents, such as antibodies, are affixed to the solid phase at different known locations, based on specificity. Because the specificity of the capture agent at each location is known, the detection of a signal at a particular location can be associated with the presence of analyte bound at that location. Examples of this format include microfluidic devices and capillary arrays, containing different capture agents at different locations along a channel or capillary, respectively, and microarrays, which typically contain different capture agents arranged in a matrix of spots ("target elements") on a surface of a solid support. In particular embodiments, each different capture agent can be affixed to a different electrode, which can, for example, be formed on a surface of a solid support, in a channel of a microfluidic device, or in a capillary.

III. Test Kits

The invention also provides test kits for assaying test samples for an immunosuppressant drug. Test kits according to the invention include one or more reagents useful for practicing one or more immunoassays according to the invention. A test kit generally includes a package with one or more containers holding the reagents, as one or more separate compositions or, optionally, as admixture where the compatibility of the reagents will allow. The test kit can also include other material(s), which may be desirable from a user standpoint, such as a buffer(s), a diluent(s), a standard(s), and/or any other material useful in sample processing, washing, or conducting any other step of the assay.

In particular embodiments, test kits of the invention can include: (a) at least one antibody capable of binding specifically to at least one immunosuppressant drug; (b) an assay diluent comprising a salt at a concentration of at least about 1.0 M; and (c) a extractive reagent comprising: a glycol selected from the group consisting of ethylene glycol, propylene glycol, and an analog thereof; and at least one alcohol having five or fewer carbons. In exemplary embodiments, the antibody can be specific for tacrolimus, everolimus, zotarolimus, cyclosporine, or analogs of any of these compounds.

The salt concentration in the assay diluent can be less than or equal to about 10.0 M, e.g., about 4.5 M. Any of the salts described above in connection with the immunoassay methods of the invention can be included in an assay diluent suitable for use in the test kits.

In certain embodiment, the extractive reagent includes methanol, ethanol, propanol, or a mixture of any of these alcohols. In exemplary embodiments, the ratio of glycol to alcohol is in the range of about 4:1 to about 1:4, more particularly, in the range of about 4:1 to about 1:2.

If desired, the test kit can additionally include a control composition that includes the immunosuppressant drug being assayed. A control composition can be included in the above-described exemplary test kit or can be included in a test kit containing, for example: (a) at least one antibody capable of binding specifically to at least one immunosuppressant drug; and (b) an assay diluent comprising a salt at a concentration of at least about 1.0 M.

Kits according to the invention can include a solid phase and a capture agent that is affixed to the solid phase or that becomes solid phase-affixed during the assay. In exemplary embodiments, the solid phase includes one or more microparticles or electrodes. Where such kits are to be employed for conducting sandwich immunoassays, the kits can additionally include a labeled detection agent. In certain embodiments, the test kit includes at least one direct label, such as acridinium-9-carboxamide. Test kits according to the invention can also include at least one indirect label. If the label employed generally requires an indicator reagent to produce a detectable signal, the test kit preferably includes one or more suitable indicator reagents.

Test kits according to the invention preferably include instructions for carrying out one or more of the immunoassays of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

Of course, it goes without saying that any of the exemplary formats herein, and any assay or kit according to the invention can be adapted or optimized for use in automated and semi-automated systems (including those in which there is a solid phase comprising a microparticle), as described, e.g., in U.S. Pat. Nos. 5,089,424 and 5,006,309, and as, e.g., commercially marketed by Abbott Laboratories (Abbott Park, Ill.) including but not limited to Abbott Laboratories' ARCHITECT®, AxSYM®, IMX®, ABBOTT PRISM®, and Quantum II platforms, as well as other platforms.

Additionally, the assays and kits of the present invention optionally can be adapted or optimized for point of care assay systems, including Abbott Laboratories'Point of Care (i-STAT®) electrochemical immunoassay system. Immunosensors and methods of manufacturing and operating them in single-use test devices are described, for example in U.S. Pat. No. 5,063,081 and published U.S. Patent Applications 20030170881, 20040018577, 20050054078, and 20060160164 (incorporated by reference herein for their teachings regarding same).

EXAMPLES

The following examples are offered to illustrate, but not to limit, the claimed invention.

Example 1

Tacrolimus Immunoassay Using Salt in the Assay Diluent

This example illustrates the effect of the addition of salt in the assay diluent in an automated immunoassay for tacrolimus.

In the current preferred assay configuration, sodium chloride (NaCl) is added to the ancillary Assay Diluent component of the ARCHITECT® Tacrolimus assay (Abbott Laboratories, Abbott Park, Ill.) at a concentration of 4.5 M. In the Tacrolimus assay, 80 µL of the Assay Diluent is combined with the microparticle reagent and the sample; the reaction volume is 180 µL, resulting in a reaction concentration of 2.0 M NaCl. After an 18 minute incubation, 20 µL of the Tacrolimus-labeled tracer reagent is added. After an additional 4 minute incubation, the microparticles are washed, then chemiluminescence triggering reagents are added and the amount of light produced (or signal) is measured as relative light units (RLUs).

RLU is the designation for the unit of optical measurement employed on the ARCHITECT® system, as well as in other instruments. The term RLU comes from the relation of the photon counting to a certain amount of signal-producing standard, such as acridinium. Each optics module is calibrated with a set of standards (e.g., acridinium standards). When the chemiluminescent reaction occurs, light is emitted and the photons are measured over a period of time (e.g., a 3 second time period). The photomultiplier tube (PMT) converts the photons counted to digital signal, which is then sent to a circuit board for processing. The optics circuit board converts the digital signal from the PMT to an analog signal that is proportional to the photons counted, which is in turn proportional to the amount of signal producing molecule (e.g., acridinium) present. This analog signal is then further processed to produce an RLU value. This relationship was established to produce a standard for calibration of the optics module, where the different standards have RLU values assigned to them. Thus, while the RLU unit itself is arbitrary, it is proportional (i.e., relative) to a certain amount of standard (e.g., acridinium).

Figure 2:
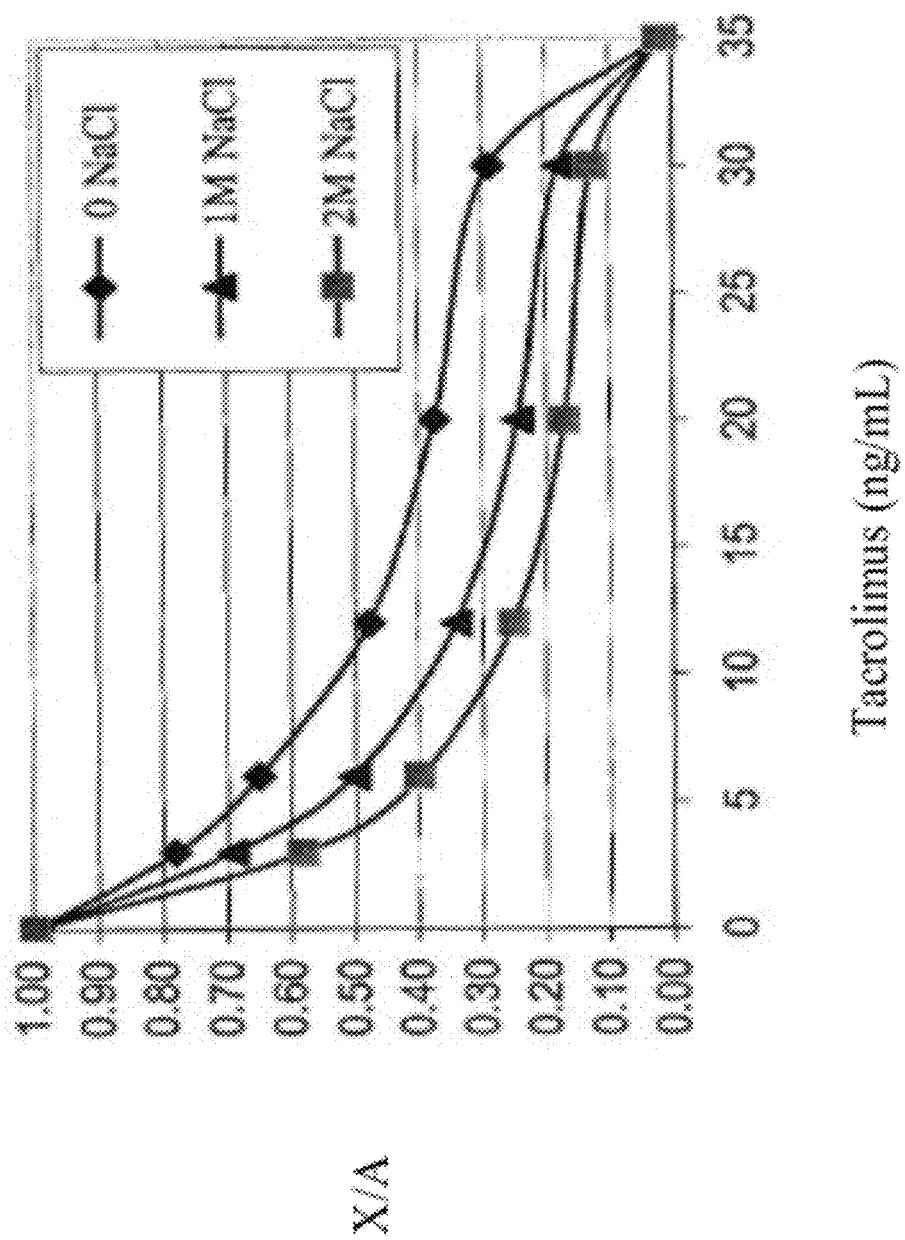
FIG. 2 is a graph obtained using an ARCHITECT® Tacrolimus Assay (Abbott Laboratories, Abbott Park, Ill.) tested with different concentrations of NaCl in the reaction. Abscissa: tacrolimus amount (ng/mL). Ordinate: X/A. Symbols: (solid diamond), 0 M NaCl; (solid triangle), 1 M NaCl; (solid square), 2 M NaCl. It can be seen that curve shape was improved (decreased B/A) by increasing NaCl concentrations in the reaction.

Results of these studies are presented in FIGS. 1 and 2.

The intensity of the tracer-produced chemiluminescent signal is inversely proportional to the concentration of unlabeled competitor tacrolimus in the sample. Addition of NaCl to the reaction mixture results in a more intense chemiluminescent signal when only Tacrolimus tracer is present in the sample. NaCl also produces a larger decrease in signal with samples containing unlabeled Tacrolimus to compete with the Tacrolimus-labeled tracer. This change allows detection of smaller amounts of tacrolimus than would be possible without the salt. Nonspecific binding (expressed as a percentage of a calibrator RLUs) is unchanged by increasing NaCl added to the reaction.

Example 2

Tacrolimus Immunoassay Using Salt in the Microparticle Reagent

This example illustrates the effect of the addition of salt in the microparticle reagent in an automated immunoassay for tacrolimus. For these assays, NaCl is added to the microparticle reagent component of the IMx® Tacrolimus II assay (Abbott Laboratories, Abbott Park, Ill.) at various concentrations.

Figure 3:
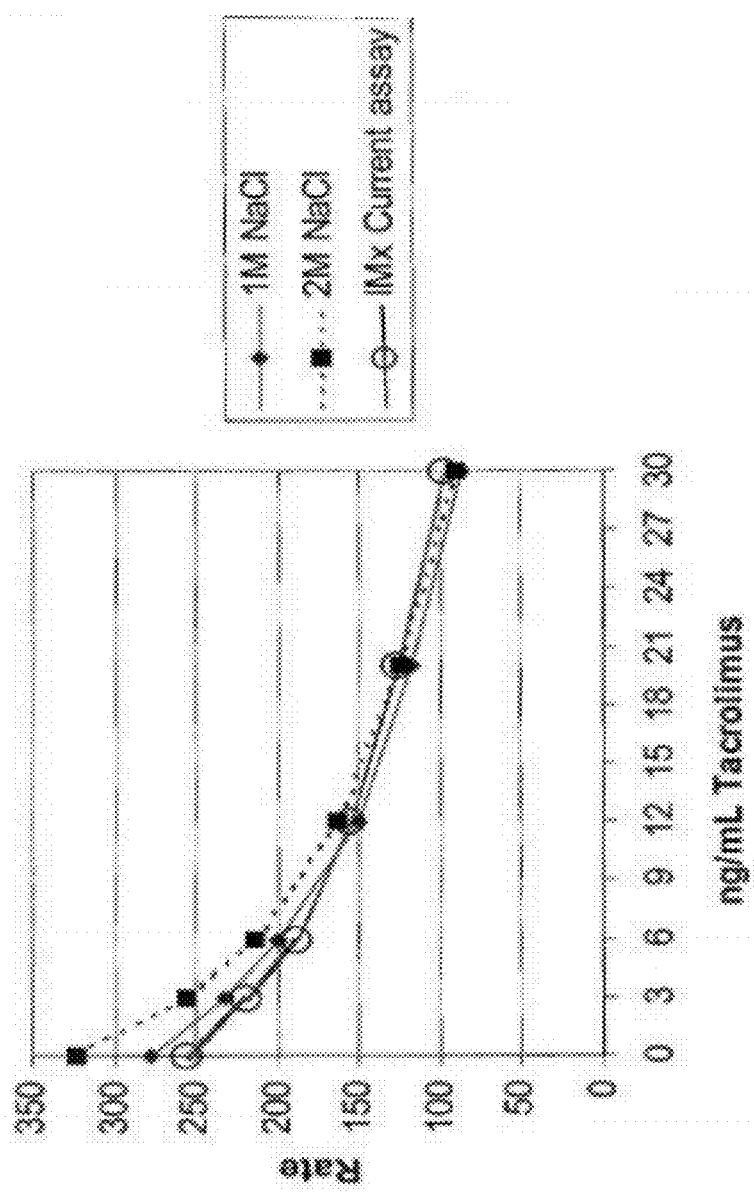
FIG. 3 is a graph obtained using an IMx® Tacrolimus II Assay (Abbott Laboratories, Abbott Park, Ill.) in which rates of blood matrix calibrators were tested with different concentrations of NaCl present in the microparticles. Abscissa: tacrolimus amount (ng/mL). Ordinate: Rate. Symbols: (solid diamond), 1 M NaCl; (solid square), 2 M NaCl; (open circle), IMx® Tacrolimus II marketed assay with no salt addition.
Figure 4:
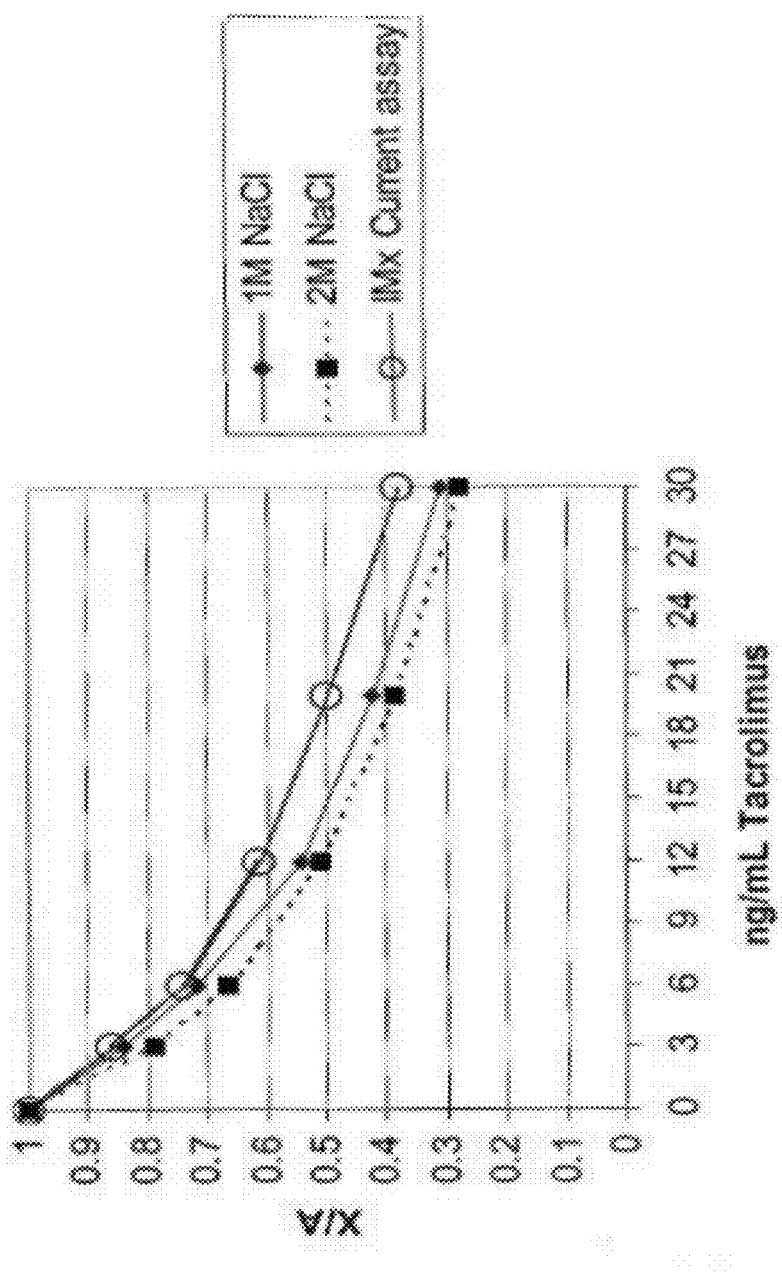
FIG. 4 is a graph obtained using an IMx® Tacrolimus H Assay (Abbott Laboratories, Abbott Park, Ill.). Abscissa: tacrolimus amount (ng/mL). Ordinate: X/A. Symbols: (solid diamond), 0 M NaCl; (solid square), 2 M NaCl; (open circle), IMx® Tacrolimus II marketed assay with no salt addition. It can be seen that curve shape was improved (decreased B/A) by 2 M NaCl concentration in the microparticles.

Results are these assays are shown in FIGS. 3 and 4. As can be seen from these Figures, addition of salt to the microparticle reagent of this assay produced a similar effect as did the addition of salt to the assay diluent in the ARCHITECT® Tacrolimus assay (FIGS. 1 and 2). This might be expected, inasmuch as the IMx®Tacrolimus II Assay extracts analyte from whole blood with a similar 75% Methanol/25% ethylene glycol/60 mM Zinc Sulfate organic mixture, and analyzes without addition of high salt (see, e.g., FIG. 3, at 0 M NaCl datapoints).

By comparison, addition of 1 M, 2 M or 4 M NaCl to the microparticle bottle of the IMx® Tacrolimus II microparticle reagent increased calibrator signal rates (see, e.g., FIG. 3, the rates of IMx® "current assay" versus the rates obtained with 1 or 2 M NaCl added), the span of rate from high to low calibrator (see, e.g., FIG. 3, the lowest and highest rates of IMx® "current assay" versus the lowest and highest rates obtained with 1 or 2 M NaCl added), sensitivity (see, e.g., FIG. 4, leftward shift of the curves for 1 or 2 M NaCl added), and performance of the assay (see, e.g., FIG. 4, calibrator X/A).

Example 3

Tacrolimus Immunoassay Using Other Salts in the Assay Diluent

This example illustrates the effect of the addition of various salts in the assay diluent in an automated immunoassay for tacrolimus.

Figure 5:
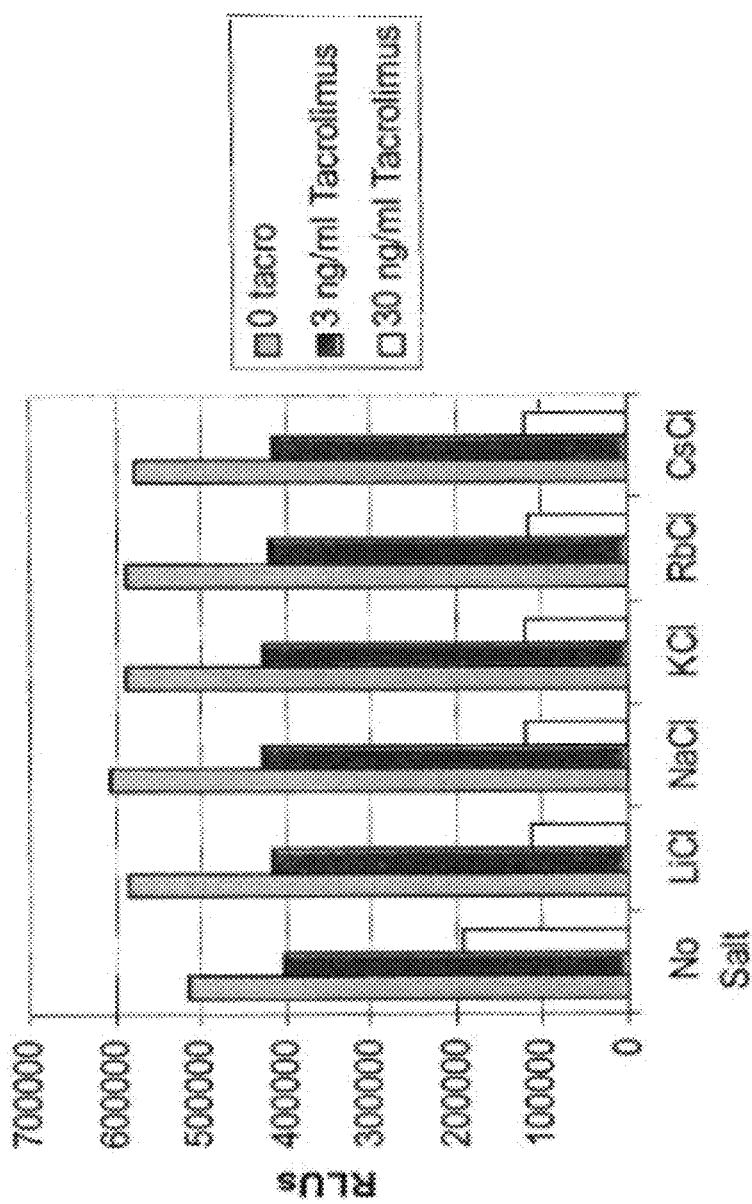
FIG. 5 is a bar chart obtained using an ARCHITECT® Tacrolimus Assay (Abbott Laboratories, Abbott Park, Ill.) and a variety of different salts at 0.44 M in each reaction. Abscissa: no salt, lithium chloride (LiCl), sodium chloride (NaCl), potassium chloride (KCl), rubidium chloride (RbCl), cesium chloride (CsCl). Ordinate: signal (RLUs). Symbols: (gray bar), 0 ng/mL tacrolimus; (black bar), 3 ng/mL tacrolimus; (open bar), 30 ng/mL tacrolimus. A minimal effect of varying alkali metals in the reaction was observed.
Figure 6:
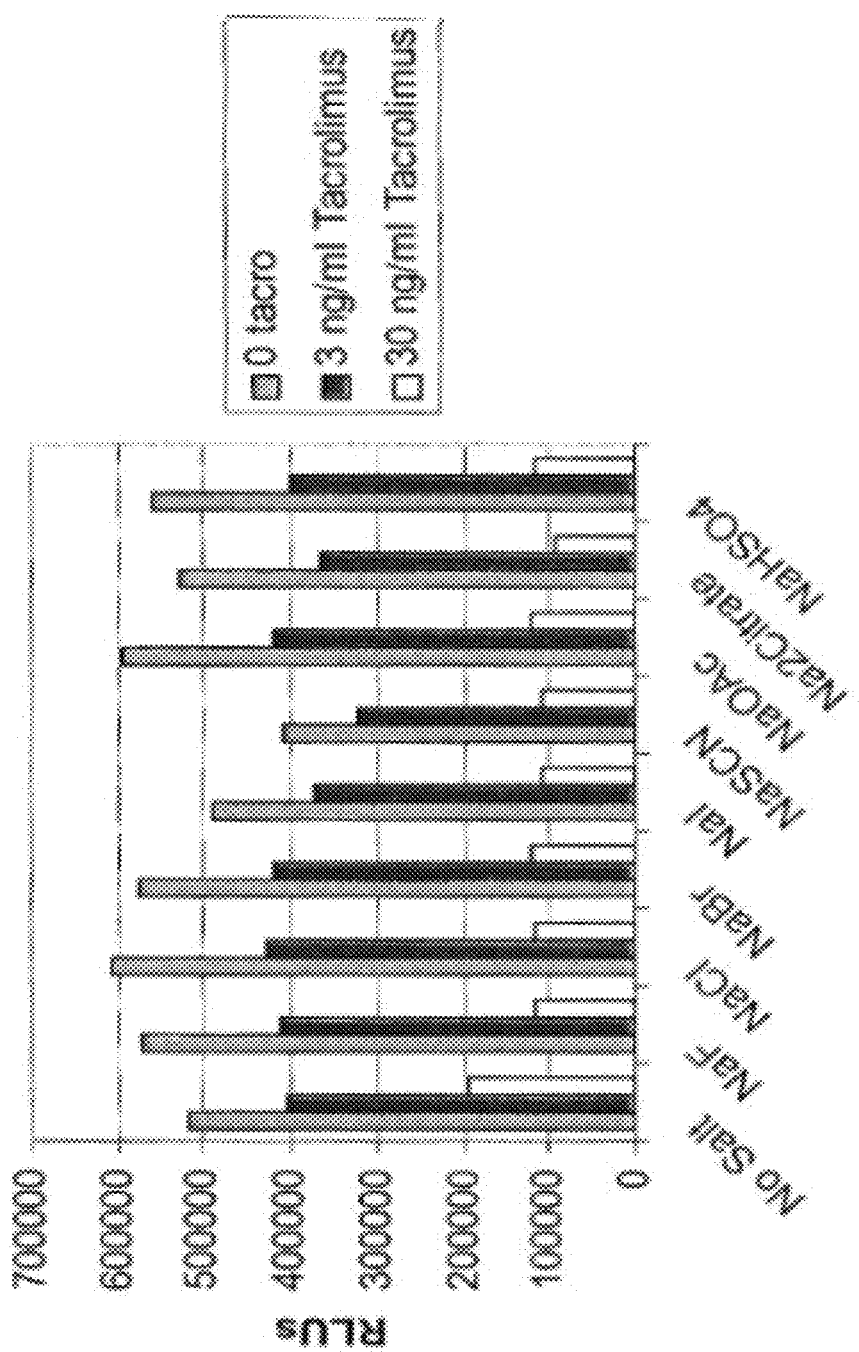
FIG. 6 is a bar chart obtained using an ARCHITECT® Tacrolimus Assay (Abbott Laboratories, Abbott Park, Ill.) and a variety of sodium salts (varying anions) at 0.44 M in each reaction. Abscissa: no salt, sodium fluoride (NaF), sodium chloride (NaCl), sodium bromide (NaBr), sodium thiocyanate (NaSCN), sodium acetate (NaOAc); sodium citrate (Na$_2$Citrate); sodium bisulfate (NaHSO$_4$). Ordinate: signal (RLUs). Symbols: (gray bar), 0 ng/mL tacrolimus; (black bar), 3 ng/mL tacrolimus; (open bar), 30 ng/mL tacrolimus. It can be seen that chloride and acetate anions produced the highest tracer binding (RLUs).

For these studies, the use of salts other than NaCl was explored. In particular the effect of varying the sodium cation and chloride anion was investigated. Results are these assays are shown in FIGS. 5 and 6. As can be seen from these Figures, salts other than NaCl produce a similar effect in the ARCHITECT® Tacrolimus assay to varying degrees. At a constant concentration (0.45 M), chloride salts of the alkali metals, Li, Na, K, Rb, and Cs all were similarly efficacious (FIG. 5). However, sodium salts or different anions behave differently (FIG. 6.). All improve assay performance, but sodium chloride was found to be highly effective and highly soluble.

It is understood that the examples and embodiments described herein are for illustrative purposes only and that various modifications or changes in light thereof will be suggested to persons skilled in the art and are to be included within the spirit and purview of this application and scope of the appended claims.

In addition, the commonly owned, co-pending application U.S. Ser. No. 60/882,732 filed on Dec. 29, 2006 is explicitly incorporated by reference in its entirety for its teachings regarding a diagnostic test for the detection of a molecule or drug in whole blood.

The commonly owned, co-pending application U.S. Provisional Application Ser. No. 60/878,017 filed on Dec. 29, 2006 is explicitly incorporated by reference in its entirety for its teachings regarding a non-denaturing lysis reagent for use with capture-in-solution immunoassay.

The commonly owned, co-pending application U.S. Nonprovisional application Ser. No. 11/618,495 filed on Dec. 29, 2006 is explicitly incorporated by reference in its entirety for its teachings regarding a non-denaturing lysis reagent.

The commonly owned, co-pending application U.S. Nonprovisional application Ser. No. 11/490,624 filed on Jul. 21, 2006 is explicitly incorporated by reference in its entirety for its teachings regarding an extractive reagent composition.

In addition, all other publications, patents, and patent applications cited herein are hereby incorporated by reference in their entirety for all purposes.

What is claimed is:

1. An assay mixture comprising:
   i) a test sample or test sample extract suspected of comprising an immunosuppressant drug;
   ii) an antibody specific for the immunosuppressant drug;
   iii) salt in a concentration of greater than about 0.45 M and less than or equal to about 4.0 M, wherein the salt comprises a monovalent or a divalent anion, wherein the assay mixture is under conditions suitable for binding of the antibody to the immunosuppressant drug, if present.

2. The assay mixture of claim 1, wherein the immunosuppressant drug is selected from the group consisting of tacrolimus, everolimus, zotarolimus, cyclosporine, and analogs of any of these compounds.

3. The assay mixture of claim 1, wherein the immunosuppressant drug comprises tacrolimus.

4. The assay mixture of claim 1, wherein the immunosuppressant drug comprises cyclosporine.

5. The assay mixture of claim 1, wherein the test sample comprises a human blood sample.

6. The assay mixture of claim 1, wherein the salt concentration is less than or equal to about 4.0 M.

7. The assay mixture of claim 1, wherein the salt concentration is about 2.0 M.

8. The assay mixture of claim 1, wherein the salt comprises a monovalent anion.

9. The assay mixture of claim 1, wherein the monovalent anion comprises chloride.

10. The assay mixture of claim 9, wherein the salt comprises a chloride salt of an alkali metal.

11. The assay mixture of claim 10, wherein the salt comprises sodium chloride.

12. The assay mixture of claim 1, wherein the assay mixture additionally comprises: a glycol selected from the group consisting of ethylene glycol, propylene glycol, and an analog thereof; and at least one alcohol having five or fewer carbons.

13. The assay mixture of claim 1, wherein the alcohol is selected from the group consisting of methanol, ethanol, and propanol.

14. The assay mixture of claim 1, wherein the ratio of glycol to alcohol is in the range of about 4:1 to about 1:4.

15. The assay mixture of claim 1, wherein the ratio of glycol to alcohol is in the range of about 4:1 to about 1:2.

16. A lysis reagent comprising:
   i) a glycol selected from the group consisting of ethylene glycol, propylene glycol, and an analog thereof; and at least one alcohol having five or fewer carbons;

ii) at least one antibody capable of binding specifically to at least one immunosuppressant drug;

iii) salt at a concentration of at least about 1.0 M and less than or equal to about 10.0 M, wherein the salt comprises a monovalent or a divalent anion.

17. The lysis reagent of claim 16, wherein the immunosuppressant drug is selected from the group consisting of tacrolimus, everolimus, zotarolimus, cyclosporine, and analogs of any of these compounds.

18. The lysis reagent of claim 16, wherein the immunosuppressant drug comprises tacrolimus.

19. The lysis reagent of claim 16, wherein the immunosuppressant drug comprises cyclosporine.

20. The lysis reagent of claim 16, wherein the salt concentration is less than or equal to about 10.0 M.

21. The lysis reagent of claim 16, wherein the salt concentration is about 4.5 M.

22. The lysis reagent of claim 16, wherein the salt comprises a monovalent anion.

23. The lysis reagent of claim 16, wherein the monovalent anion comprises chloride.

24. The lysis reagent of claim 23, wherein the salt comprises a chloride salt of an alkali metal.

25. The lysis reagent of claim 24, wherein the salt comprises sodium chloride.

26. The lysis reagent of claim 16, wherein the alcohol is selected from the group consisting of methanol, ethanol, and propanol.

27. The lysis reagent of claim 16, wherein the ratio of glycol to alcohol is in the range of about 4:1 to about 1:4.

28. The lysis reagent of claim 16, wherein the ratio of glycol to alcohol is in the range of about 4:1 to about 1:2.

* * * * *